United States Patent [19]

Peterson

[11] Patent Number: 4,491,012

[45] Date of Patent: * Jan. 1, 1985

[54] METHOD FOR MEASURING ERYTHROCYTE DEFORMABILITY

[75] Inventor: David D. Peterson, Pleasanton, Calif.

[73] Assignee: Nuclepore Corp., Pleasanton, Calif.

[*] Notice: The portion of the term of this patent subsequent to Sep. 6, 2000 has been disclaimed.

[21] Appl. No.: 432,635

[22] Filed: Oct. 4, 1982

[51] Int. Cl.³ ............................................. G01N 33/48
[52] U.S. Cl. ...................................... 73/61.4; 422/55; 436/63; 436/70
[58] Field of Search ................ 55/158; 73/61 R, 61.4; 210/490, 491, 500.2; 356/38, 39, 42; 422/55, 56, 57, 101; 436/63, 70, 177

[56] References Cited

U.S. PATENT DOCUMENTS 3,677,844  7/1972  Fleischer et al. ................. 55/158 X
4,402,216  9/1983  Peterson ................................. 73/61.4

FOREIGN PATENT DOCUMENTS 2431129  3/1980  France ................................. 73/61.4

OTHER PUBLICATIONS

Tannert et al., Chemical Abstracts, vol. 95, #95: 183459k (11/23/81).
Maeda et al., Chemical Abstracts, vol. 93, #93: 129616e (1980).
Rampling, Chemical Abstracts, vol. 83, #145201q, (1975).

Primary Examiner—Barry S. Richman
Assistant Examiner—Robert J. Hill, Jr.
Attorney, Agent, or Firm—Flehr, Hohbach, Test, Albritton & Herbert

[57] ABSTRACT

A method and means for measuring erythrocyte deformability is provided comprising an absorbent strip and a filter membrane, the membrane characterized by pores having a mean pore size in the range of 3.0 to 8.0 microns, the membrane and the strip being in at least partial cofacial contact. A 10 microliter sample of blood is drawn through the membrane by capillary action and flows along the absorbent strip. The time required for the blood to traverse a predetermined lateral distance along the strip is recorded.

2 Claims, 3 Drawing Figures

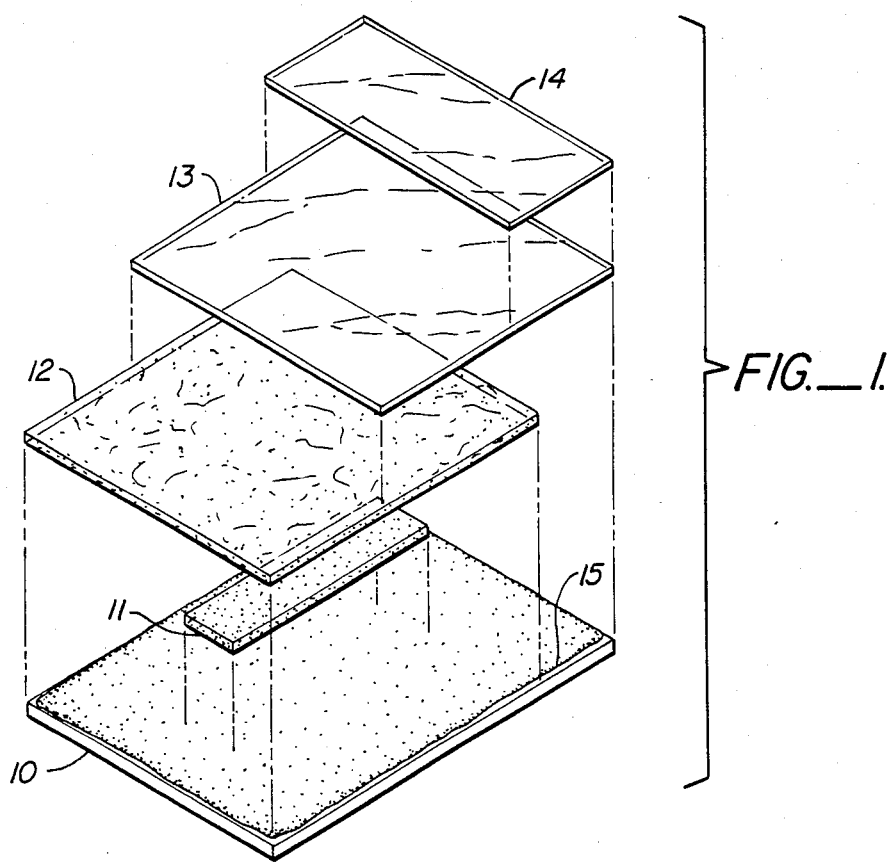
FIG._1.
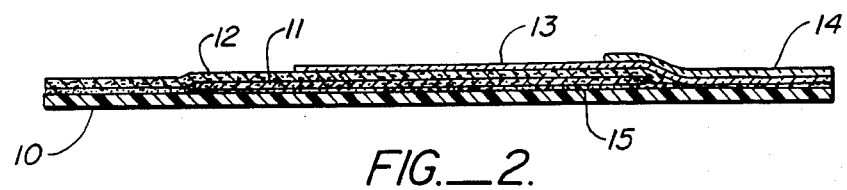
FIG._2.
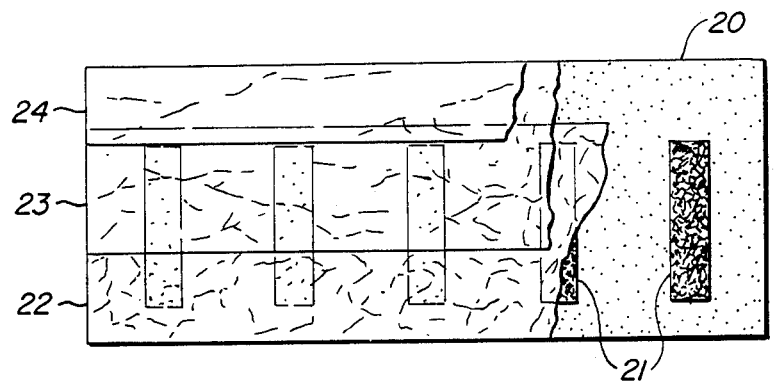
FIG._3.

METHOD FOR MEASURING ERYTHROCYTE DEFORMABILITY

The present invention is directed to a method and means for rapid, quantitative measurement of the level of deformability of human red blood cells (erythrocytes). The present invention is further directed to a method and means for rapidly measuring the relative viscosity of fluids.

The degree of deformability of erythrocytes is a critical parameter for the proper function of the erythrocytes, particularly with respect to oxygenation of tissues and for removal of metabolites, both of which occur primarily in the capillaries of the peripheral circulatory system. It is known that a healthy erythrocyte has a mean diameter of about 7.5 microns and is able to deform without hemolysis to pass through capillaries as small as 3 microns in diameter. Since decreased erythrocyte deformability is coincident with many diseases, for example, sickle cell anemia, diabetes and various cardiovascular diseases, the ability of erythrocytes to pass through capillaries may be used as a measure of deformability, and in turn, as an indication of diseased cells.

It is known that in order for healthy erythrocytes to pass through the microcirculatory capillary system within the body they need to undergo a considerable deformation. Lessin et al. (Blood Cells 3, 241-262, 1977) discloses that normal human erythrocytes demonstrate a greater deformability than cells with the sickle cell trait, hereditary spherocytosis or sickle cell anemia. The method of measuring deformability of erythrocytes disclosed by Lessin et al. is to filter a suspension of erythrocytes through a microfilter under a positive pressure cell filtration system and to subsequently measure the resistance of the suspension to flow across the micropore filter by pressure change induced by varying the flow rate. However, the system disclosed by Lessin et al. is complex, expensive, and time consuming.

Reid et al. (J. Clin. Pharm. 29, 855-858, 1976) disclose the measurement of the deformability index of red blood cells in terms of volume of red blood cells filtered through a membrane filter per minute. The system disclosed by Reid et al. calls for the use of whole blood and the filtration must be induced by negative pressure to draw the blood through the membrane filter. The system is expensive in that a vacuum device is required, and is relatively time consuming and inconvenient, particularly since there may be a variation in pressure drop during the course of filtration which affects the accuracy of measurement. The system of Reid et al. therefore requires constant attention to the suction device in order to attempt to maintain a relatively constant negative pressure.

Other methods used to measure deformability include a micropipette method by Rand (*Biophysics Journal*, 4, 155, 1964) and a laser defraction instrument called an ektacytometer disclosed by Bessis and Mohandas (*Blood Cells* 1, 307-314, 1975). Other instruments for measuring deformability include the erythrocyte rigidometer, an optical microscopic instrument disclosed by Kiesewetter (*Scand. J. Clin. Lab. Invest.* 41, 229-232 1981).

In copending commonly assigned U.S. application Ser. No. 298,195, filed Aug. 31, 1981, now U.S. Pat. No. 4,402,216, there is disclosed an erythrocyte deformability monitor comprising a series of special filters with different pore sizes whereby the red blood cells are absorbed through the filters onto an absorptive material behind the filters.

Except for the method disclosed in copending U.S. Ser. No. 298,195, all of the above methods involve a variety of special equipment and accessories, which may be complex and expensive. The erythrocyte filtration device according to the present invention is advantageous since it eliminates special electronic equipment and accessories.

While the method disclosed in copending U.S. Ser. No. 298,195 does not use specialized expensive equipment, the method disclosed therein includes a complicated configuration compared to the present invention.

The method in the copending aforementioned application includes a series of filters with different pore sizes and permits a qualitative method of deformability. The present device is advantageous since it permits quantitative measurement of fluid flow rate, particularly an erythrocyte containing fluid, through a filter membrane with high precision and accuracy.

It is an object of the present invention to provide a simple, rapid and convenient method for quantitatively evaluating the deformability of healthy and disease erythrocytes.

It is a further object of the present invention to provide a device for quantitatively measuring the deformability of erythrocytes which is completely self-contained and disposable.

It is a further object of the present invention to provide a device for quantitatively measuring the deformability of erythrocytes which device employs a single filter and which allows quantitative measurement of fluid flow rate, particularly fluid containing erythrocytes.

According to the present invention, the fluid flow rate, and particularly the deformability of erythrocytes, may be measured by placing a sample of the fluid, in particular blood, onto a membrane characterized by pores having a mean pore size in the range of 3.0 to 8.0 microns whereby the fluid (blood) filters through the membrane by capillary action and onto an absorbent strip in at least partial cofacial contact with the membrane and flows a predetermined distance along the absorbent strip, and measuring the time required for the fluid (blood) to traverse the predetermined distance along the strip.

FIG. 1 is an exploded view of a test strip in accordance with the present invention.

FIG. 2 is an elevation of the assembled test strip of FIG. 1.

FIG. 3 is a plan view of a test strip according to the present invention accommodating a plurality of absorbent strips.

The device according to the present invention is preferably utilized for investigations of the filterability of red blood cells, however it is generally applicable for measuring the flow rate of any fluid to determine fluid viscosity.

The volume of fluid sample, in particular blood, required to operate the device according to the present invention is approximately ten microliters. This is an advantage over conventional blood filtration measurement devices which require sample volumes in the range of 100 microliters.

The device according to the present invention comprises an absorbent strip and a membrane which are at least in partial cofacial contact with one another. The membrane is a thin film with a sharply defined pore size distribution. The preferred membrane is a unique thin polycarbonate film, approximately 10 microns in thickness, perforated with capillary shaped pores with a sharply defined pore size distribution and made according to the process disclosed in U.S. Pat. No. 3,303,085. The membrane is available from Nuclepore Corporation, Pleasanton, Calif. under the name Hema-fil TM. While the mean pore size of the membrane may be in the range of 3.0 to 8.0 microns, the preferred mean pore size is approximately 5 microns.

Pores in the Hema-fil TM membranes are straight through and normal (within ±34°) to the surface with evenly random disperson over the surface. Such precise pore geometry contributes to uniform sample deposition over the membrane surface and makes possible reliable particle size separation by serial filtration. Since such membranes are manufactured by the two-step process as described in U.S. Pat. No. 3,303,085, then can be made with specific mean pore sizes and densities. Actual maximum pore diameter in Hema-fil TM membranes is 4.7±0.2 microns.

The thickness of Hema-fil TM membranes varies less than 5% from a nominal thickness of 10 microns. The pore density (pores/cm$^2$) and pore diameter of Hema-fil TM membranes are controlled closely and uniquely to provide the best combination of strength and flow rate. Pore density range is $4.0 \times 10^5 (\pm 15\%)$ pores/cm$^2$. The membranes are flexible and are not easily split, having a tensile strength of at least 3000 psi. The membranes have a very low, constant tare weight. For a given pore size, weight varies no more than ±5%. Pore sizes 3.0 through 8.0 microns have nominal weights of 1 mg/cm$^2$. The membranes are readily wet with water and many other fluids, and are neither bacateriostatic nor batericidal. The specific gravity of the Hema-fil TM membranes is in the range of 0.94 to 0.97 gm/cc and the membranes may withstand temperatures as high as 140° C. indefinitely without adverse affects.

The absorbent strip may be any absorbent material which exhibits uniform absorption at a reproducible rate and which preferably permits facile lateral flow of red blood cells. Preferably the absorbent strip is filter paper, but may also be a synthetic material such as absorbent plastic, and the like. The flow rate along the absorbent strip depends on the width of the strip and it is preferred that the absorption front has a width of less than about 3 millimeters for use in analyzing the deformability of blood.

The device is used to measure the time interval of the fluid sample, such as the sample of blood, required to absorb along the length of the absorbent strip. A timer is started upon placement of the sample on the membrane at the portion at which it is in cofacial contact with the absorbent strip. The timer is stopped when the blood reaches the opposite end of the strip. The same procedure may be repeated using a blood sample on a plurality of strips, after which the mean absorption time is calculated for the plurality of values.

Referring to FIGS. 1 and 2 there, is shown one embodiment of the device according to the present invention. As shown in FIG. 1 the device has a flat rectangular shape and shows a base layer 10, absorbent strip 11, filter membrane 12, a transparent tape layer 13 and an opaque cover tape layer 14. The base layer 10 supports the device and is preferably opaque and coated with a pressure sensitive adhesive on one surface. Base layer 10 may also be preferably colored in order to create a contrasting background to enhance the visibility of absorbent strip 11. The absorbent strip 11 and filter membrane 12 bond to the adhesive surface 15 of the base layer 10. The filter membrane 12 overlays the absorbent strip 11. A transparent tape layer 13 overlays a portion of the filter membrane 12 and absorbent strip 11 and defines an area of exposed filter membrane at one end of the absorbent strip. An opaque tape cover layer 14 overlays the transparent tape layer 13 and defines the top end (the terminal end of the absorbent strip) of the absorbent strip 11.

Referring to FIG. 3 there is shown another embodiment having a base layer 20 and a plurality of absorbent strips 21. A common filter membrane 22, tape layer 23 and cover tape layer 24 are respectively fixed as described above in connection with FIGS. 1 and 2.

The device is activated by placing a small volume (approximately 10 microliters) of a sample fluid, usually blood, onto the filter membrane which is in partial cofacial contact with one end of the absorbent strip. Shortly after activation the fluid front (blood) is observed moving along absorbent strip 11. As the fluid advances along the strip the absorption front is visible even for clear fluids. The time interval required for fluid to absorb to the end of the absorbent strip is a readout from the device and is timed by the user. The fluid flow rate is calculated from the absorbed fluid volume and the absorption time interval.

The device according to the present invention differs in its basic principle of operation in some important ways from standard filtration systems. Firstly, the driving force is due to the capillary forces in the absorbent strip. Secondly, the length of the fluid flow path along the absorbent strip increases with time. As a result, the effective pressure gradient acting in the system decreases monotonically as flow progresses. The consequences of a decreasing pressure gradient creates certain basic differences in the dynamics of fluid flow in the present device compared to systems with a constant pressure gradient. Fluid flow rate in the device according to the present invention depends on the inverse of the fluid volume absorbed and the fluid absorbed is directly proportional to square root of absorption time. The time required to absorb a given volume depends on the square of the volume absorbed. Therefore, due to these relationships the initial flow rate is high but diminishes rapidly with time.

Evaluation of the performance of the erythrocyte filtration device according to the present invention may be made with normal and diseased human blood samples. The device used in these evaluations has a plurality of absorbent strips designed as shown in FIG. 3. The device consists of 5 absorbent strips with a width and length, respectively of 3.38±0.16 millimeters and 9.76±0.04 millimeters. The ends of the absorbent strips are overlayed with a Nuclepore Hema-fil TM membrane, a polycarbonate, capillary-pore membrane with a pore size of 4.7±0.2 microns; density $4 \times 10^5$ pores/centimeters$^2$, and membrane thickness of 10.3±0.3 microns. The mean length and area of the overlayed ends of the strips is 3.34±0.09 millimeters and 11.3±0.6 millimeters$^2$, respectively. The overall dimensions of the device in FIG. 3 are 38 millimeters by 76 millimeters. The mean absorbent capacity of each strip is 5.3 microliters.

Test results with normal blood are shown in Table 1 below and show that the mean absorption time ($T_a$) depends strongly on the hematocrit (H). Hematocrit is the concentration expressed as volume % of red blood cells in the suspending medium. The mean absorption time exhibits an exponential dependence on hematocrit for H greater than or equal to 5%. A graph of $LnT_a$ versus H would yield a straight line for H greater or equal to 8.8% for the values listed in Table 1. The mean absorbed times in Table 1 may be calculated by the following equation:

$$T_a = K \exp(0.055H) \tag{1}$$

where H is in % and $T_a$ is in seconds. The value of K is listed in column 4 of Table 1. K is calculated from the equation:

$$K = T_a \exp(-0.055H) \tag{2}$$

and has the units of seconds. For H greater or equal to 5% in Table 1, the average K value is $4.4 \pm 0.4$ seconds. The K parameter will be shown to be a highly significant parameter for a given blood sample.

In each case, a 10 microliter sample of blood was applied to a device according to FIG. 1, employing a Hema-fil ™ membrane filter. The absorbent strip was Whatman filter paper, No. 41.

TABLE 1

MEAN ABSORB TIME AND K AS FUNCTION OF HEMATOCRIT

| Sample | H (%) | $T_a$ (sec) | $K^b$ (sec) |
|---|---|---|---|
| PBS[a] | — | 2.6 ± −0.4 | 2.6 ± −0.4 |
| AA[c] | 0.8 | 2.8 ± −0.3 | 2.7 ± −0.3 |
| AA | 1.1 | 2.8 ± −0.3 | 2.6 ± −0.3 |
| AA | 2.5 | 3.9 ± −0.5 | 3.4 ± −0.4 |
| AA | 8.8 | 8.1 ± −0.5 | 5.0 ± −0.3 |
| AA | 19.3 | 10.9 ± −0.6 | 3.8 ± −0.2 |
| AA | 28.5 | 21.9 ± −1.9 | 4.6 ± −0.4 |
| AA | 31.0 | 25.3 ± −2.1 | 4.6 ± −0.4 |
| AA | 39.0 | 37.0 ± −4.1 | 4.3 ± −0.5 |
| AA | 51.3 | 70 ± −8 | 4.2 ± −0.4 |

[a] phosphate buffered saline
[b] $K = T_a \exp(-0.055H)$
[c] fresh AA blood, diluted with PBS The red blood cell suspensions used in obtaining the results of Table 1 were prepared with normal (AA) blood from a healthy donor. The blood sample was drawn by venepuncture and anticoagulated with EDTA (ethylenediaminetetraacetate). The red cell fraction was collected by centrifugation and washed in phosphate buffered saline. Red cell suspensions at different hematocrits were prepared by dilution with phosphate buffered saline.

The relationship between mean absorb time ($T_a$) and hematocrit (H) shown by equation (1) above is found to describe results for both normal and diseased erythrocytes. The value 0.055 in the exponent in equation 1 is the slope of a straight in a graph of $LnT_a$ versus H. The same value, 0.055, is found for both normal and diseased erythrocytes. The significance is that the parameter K given by equation (2) uniquely specifies the filterability and therefore the deformability of the red blood cells. In practice of the invention, the erythrocyte filtration device is used to measure the mean absorb time ($T_a$) for a given blood sample. The hematocrit (H) of the sample must be measured independently by known techniques. The K parameter is then calculated by a substitution of $T_a$ and H into equation 2. The value of K is unique for the given blood sample and defines filterability or deformability of the red blood cells.

Table 2 below lists test results obtained with the erythrocyte filtration device for normal and diseased blood samples. The first and second columns list, respectively, a sample number and identification, the third column measured hematocrit, and the fourth column lists the mean absorb time, the fifth column lists the calculated K. The footnotes in Table 2 indicate details regarding the blood samples.

TABLE 2

RESULTS FOR NORMAL AND DISEASED ERYTHROCYTES MEASURED WITH ERYTHROCYTE FILTRATION DEVICE

| # | Sample | H (%) | $T_a$ (sec) | K* (sec) |
|---|---|---|---|---|
| 1 | AAFA | 43.0 | 15.7 ± 0.8 | 1.5 ± 0.1 |
| 2 | AAFB | 38.5 | 25 ± 6 | 3.1 ± 0.7 |
| 3 | AAFPBS | 39.0 | 37 ± 3 | 4.3 ± 0.4 |
| 4 | AA1 | 36.8 | 19.7 ± 1.6 | 2.6 ± 0.2 |
| 5 | AA30 | 50.0 | 138 ± 15 | 8.8 ± 1.0 |
| 6 | AA30PBS | 35.8 | 19.6 ± 2.3 | 2.7 ± 0.3 |
| 7 | SC1 | 27.7 | 27.3 ± 3.3 | 6.0 ± 0.7 |
| 8 | SC7 | 26.3 | 224 ± 27 | 53 ± 6 |
| 9 | D2 | 35.6 | 25.0 ± 3.7 | 3.5 ± 0.5 |
| 10 | D7A | 47.5 | 425 ± 54 | 31 ± 4 |
| 11 | D7B | 44.0 | 323 ± 43 | 29 ± 4 |
| 12 | SSF | 24.0 | 260 ± 21 | 69 ± 6 |
| 13 | SSFPBS | 15.0 | 163 ± 25 | 71 ± 11 |
| 14 | SSFC | 32.0 | 362 ± 34 | 62 ± 6 |
| 15 | SS1DMA | 26.5 | 122 ± 35 | 28 ± 8 |
| 16 | SSFDMA | 25.0 | 292 ± 34 | 74 ± 9 |
| 17 | SS1PG | 24.0 | 512 ± 85 | 137 ± 23 |

*K = $T_a \exp(-0.055H)$
1. Normal, fresh, whole, male, oriental.
2. Normal, fresh, whole, female, caucasian.
3. (2.) concentrated, washed, suspended in phosphate buffered saline.
4. Normal, 1 day old, whole.
5. Normal, 30 day old, whole expired blood from blood bank.
6. (5.) - diluted with phosphate buffered saline (PBS).
7. Sickle-trait, 1 day old, whole.
8. Sickle-trait, 7 days old, whole.
9. Diabetes, 2 days old, whole.
10. Diabetes, 7 days old, whole, patient A.
11. Diabetes, 7 days old, whole, patient B.
12. Sickle-cell, fresh, whole.
13. (12.) diluted with PBS.
14. (12.) concentrated by centrifugation.
15. Sickle-cell, 1 day old, treated with anti-sickling agent (−14 days DMA).
16. Sickle-cell, fresh, anti-sickling agent DMA (−42 days).
17. Sickle-cell, 1 day old, female, pregnant.

The results listed in Table 2 show that the K value for normal blood (AA) falls into the range 1.5 to 4 seconds. Sickle-cell diseased blood exhibits K values in the range of 65 to 140 seconds. Thus in general, diseased blood is characterized by high K values, normal blood by low K values. The data in Table 2 illustrates the importance of the conditions of the blood samples regarding type of disease, age of sample, prior drug treatment, time administration and whether the sample is whole or diluted.

It is noted that for H=0 equation 1 yields the relationship $T_a = K$. Therefore K is simply the mean absorb time at H=0 and thus the point of intercept of the $T_a$ (H) curve on the $T_a$ axis.

A comparison of results with the erythrocyte filtration device and the standard filtration method is presented in Table 3 below.

TABLE 3

Results Of Comparison Of Erythrocyte Filtration Method With Pressure Filtration Method

| Sample | (%) | $T_a^a$ (sec) | $T_D^b$ (sec) | $T_a/T_D$ |
|---|---|---|---|---|
| PBS | — | 2.6 ± 0.4 | 2.5 ± 0.1 | 1.0 |
| AA | 8.8 | 8.1 ± 0.5 | 4.7 | 1.7 |
| AA | 19.3 | 10.9 ± 0.6 | 8.4 | 1.3 |
| AA | 28.5 | 21.9 ± 1.9 | 14.3 | 1.5 |

TABLE 3-continued

Results Of Comparison Of Erythrocyte Filtration
Method With Pressure Filtration Method

| Sample | (%) | $T_a{}^a$ (sec) | $T_D{}^b$ (sec) | $T_a/T_D$ |
|---|---|---|---|---|
| AA | 31.0 | 25.3 ± 2.1 | 14.1 | 1.8 |
| AA | 39.0 | 37.0 ± 4.1 | 22.3 | 1.7 |
| AA | 51.3 | 70 ± 8 | 54.0 | 1.3 |

$^a$Erythrocyte filtration method
$^b$Pressure filtration method

The filtration method used the same Nuclepore Hemafil TM membrane filter described hereinabove. In the filtration method, the drain time $T_D$ was recorded between the first and second drops under gravity feed at the outlet of the filter holder. A sample volume of 200 microliters was poured over the surface of the 13 mm diameter filter. The volume of a droplet is approximately 66 microliters. The filtration drain time results show a strong dependence on hematrocrit, a result which is expected. The fifth column lists the ratio of the mean absorb time to the filtration drain time, $T_a/T_D$. This ratio is nearly constant, and has an average value of 1.5±0.2. The results in Table 3 may be interpreted as showing that the absorb filtration device yields the exact same results as obtained by the standard filtration method.

What is claimed is:

1. A method of measuring erythrocyte deformability comprising the steps of placing a sample of blood of predetermined hematocrit onto a membrane characterized by capillary shaped pores having a mean pore size in the range of 3.0 to 8.0 microns, whereby blood filters through said membrane by capillary action and onto an absorbent strip in at least partial cofacial contact with said membrane, and flows a predetermined lateral distance along said absorbent strip, measuring the time required for the blood to traverse said predetermined lateral distance, and calculating the erythrocyte deformability from said time and said hematocrit; said membrane characterized by straight through pores substantially normal to the surface of said membrane, a pore density of $4.0 \times 10^5 \pm 15\%$ pores/cm$^2$, a tensile strength of at least 3000 psi, and a specific gravity in the range of 0.94 to 0.97 gm/cc.

2. A method according to claim 1 wherein the said mean pore size is 4.7±0.2 microns.

* * * * *